United States Patent
Min

(10) Patent No.: US 10,207,044 B2
(45) Date of Patent: Feb. 19, 2019

(54) FIVE-PORT BLOOD SEPARATION CHAMBER AND METHODS OF USING THE SAME

(71) Applicant: Fenwal, Inc., Lake Zurich, IL (US)

(72) Inventor: Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 147 days.

(21) Appl. No.: 15/221,657

(22) Filed: Jul. 28, 2016

(65) Prior Publication Data

US 2017/0028122 A1 Feb. 2, 2017

Related U.S. Application Data

(60) Provisional application No. 62/198,369, filed on Jul. 29, 2015.

(51) Int. Cl.
*A61M 1/36* (2006.01)
*A61M 1/38* (2006.01)
*B04B 11/02* (2006.01)
*B04B 11/06* (2006.01)
*B04B 5/04* (2006.01)

(52) U.S. Cl.
CPC ........ *A61M 1/3696* (2014.02); *A61M 1/3693* (2013.01); *A61M 1/38* (2013.01); *B04B 5/0442* (2013.01); *B04B 11/02* (2013.01); *B04B 11/06* (2013.01)

(58) Field of Classification Search
CPC .... A61M 1/3693; A61M 1/3696; A61M 1/38; B04B 11/02; B04B 11/06; B04B 5/0442
See application file for complete search history.

(56) References Cited

U.S. PATENT DOCUMENTS

| | | |
|---|---|---|
| 4,120,449 A | 10/1978 | Brown et al. |
| 4,386,730 A | 6/1983 | Mulzett |
| 4,387,848 A | 6/1983 | Melroy |
| 4,419,089 A | 12/1983 | Kolobow et al. |
| 4,647,279 A | 3/1987 | Mulzet et al. |
| 4,708,712 A | 11/1987 | Mulzet |
| 4,851,126 A | 7/1989 | Jones |
| 4,934,995 A | 6/1990 | Cuilis |

(Continued)

FOREIGN PATENT DOCUMENTS

| | | |
|---|---|---|
| WO | WO 9633023 A1 | 10/1996 |
| WO | WO 9850163 A1 | 11/1998 |

(Continued)

OTHER PUBLICATIONS

Extended European Search Report for European Patent No. 16181726.7, dated Dec. 20, 2016.

*Primary Examiner* — John Kim
(74) *Attorney, Agent, or Firm* — Cook Alex Ltd.

(57) ABSTRACT

Systems and methods are provided for separating blood into two or more separated blood components. The system includes a blood separation chamber with a single stage having five ports connected thereto. The five ports include a blood inlet port, a red blood cell outlet port, a platelet-rich plasma outlet port, a platelet-poor plasma outlet port, and a buffy coat outlet port. In the single stage, blood may be separated into a variety of components, such as red blood cells and platelet-rich plasma or red blood cells, platelet-poor plasma, and buffy coat. Depending on the components into which the blood is to be separated, flow out of one or more of the outlet ports may be prevented.

7 Claims, 7 Drawing Sheets

(56) References Cited

U.S. PATENT DOCUMENTS

| | | |
|---|---|---|
| 5,217,426 A | 6/1993 | Bacehowski et al. |
| 5,370,802 A | 12/1994 | Brown |
| 5,632,893 A | 5/1997 | Brown et al. |
| 5,649,903 A | 7/1997 | Deniega |
| 5,674,173 A | 10/1997 | Hlavinka |
| 5,722,926 A | 3/1998 | Hlavinka |
| 5,868,696 A | 2/1999 | Giesler |
| 5,906,570 A | 5/1999 | Langley |
| 5,913,768 A | 6/1999 | Langley |
| 5,939,319 A | 8/1999 | Hlavinka |
| 5,951,877 A | 9/1999 | Langley et al. |
| 5,993,370 A | 11/1999 | Brown |
| 5,996,634 A | 12/1999 | Dennehey |
| 6,022,306 A | 2/2000 | Dumont et al. |
| 6,051,146 A | 4/2000 | Green |
| 6,053,856 A | 4/2000 | Hlavinka |
| 6,071,422 A | 6/2000 | Hlavinka |
| 6,254,784 B1 | 7/2001 | Nayak et al. |
| 6,277,060 B1 | 8/2001 | Neumann |
| 6,312,607 B1 | 11/2001 | Brown et al. |
| 6,334,842 B1 | 1/2002 | Sorkin |
| 6,348,156 B1 | 2/2002 | Vishnoi |
| 6,582,349 B1 | 6/2003 | Cantu |
| 6,793,828 B2 | 9/2004 | Dolecek et al. |
| 6,875,191 B2 | 4/2005 | Smith |
| 7,011,761 B2 | 3/2006 | Muller |
| 7,087,177 B2 | 8/2006 | Min |
| 7,297,272 B2 | 11/2007 | Min |
| 7,354,415 B2 | 4/2008 | Bainbridge et al. |
| 7,438,679 B2 | 4/2008 | Hlavinka et al. |
| 7,442,178 B2 | 10/2008 | Chammas |
| 7,452,322 B2 | 11/2008 | Headley et al. |
| 7,470,371 B2 | 12/2008 | Dorian et al. |
| 7,473,216 B2 | 1/2009 | Lolachi et al. |
| 7,497,944 B2 | 3/2009 | Hogberg et al. |
| 7,549,956 B2 | 6/2009 | Hlavinka et al. |
| 7,582,049 B2 | 9/2009 | Hlavinka et al. |
| 7,588,692 B2 | 9/2009 | Antwiler et al. |
| 7,601,268 B2 | 10/2009 | Ragusa |
| 7,648,452 B2 | 1/2010 | Holmes et al. |
| 7,648,639 B2 | 1/2010 | Holmes et al. |
| 7,674,221 B2 | 3/2010 | Hudock et al. |
| 7,708,152 B2 | 5/2010 | Dorian et al. |
| 7,708,710 B2 | 5/2010 | Min |
| 7,766,809 B2 | 8/2010 | Dolecek et al. |
| 7,811,463 B2 | 10/2010 | Dolecek et al. |
| 7,819,793 B2 | 10/2010 | Lindell et al. |
| 7,824,559 B2 | 11/2010 | Dorian et al. |
| 7,833,185 B2 | 11/2010 | Felt et al. |
| 7,837,884 B2 | 11/2010 | Dorian et al. |
| 7,857,744 B2 | 12/2010 | Langley et al. |
| 7,866,485 B2 | 1/2011 | Dorian et al. |
| 7,867,159 B2 | 1/2011 | Dolecek et al. |
| 7,981,019 B2 | 3/2011 | Holmes et al. |
| 7,934,603 B2 | 5/2011 | Eaton et al. |
| 7,943,916 B2 | 5/2011 | Carter et al. |
| 7,963,901 B2 | 6/2011 | Langley et al. |
| 7,976,796 B1 | 7/2011 | Smith et al. |
| 7,987,995 B2 | 8/2011 | Dorian et al. |
| 8,012,077 B2 | 9/2011 | Hoeppner |
| 8,057,377 B2 | 11/2011 | Holmes et al. |
| 8,075,468 B2 | 12/2011 | Min |
| 8,556,793 B2 | 10/2013 | Foley et al. |
| 2003/0066807 A1 | 4/2003 | Suzuki |
| 2003/0166445 A1 | 9/2003 | Rochat |
| 2003/0173274 A1 | 9/2003 | Corbin, III et al. |
| 2004/0065626 A1 | 4/2004 | Woo |
| 2008/0147240 A1 | 6/2008 | Hudock et al. |
| 2008/0149564 A1 | 6/2008 | Holmes |
| 2008/0153686 A1 | 6/2008 | Rochat |
| 2008/0171646 A1 | 7/2008 | Dolecek et al. |
| 2008/0248938 A1 | 10/2008 | Chammas |
| 2008/0283473 A1 | 11/2008 | Holmes et al. |
| 2009/0259162 A1 | 10/2009 | Ohashi et al. |
| 2009/0272701 A1 | 11/2009 | Holmes et al. |
| 2009/0286221 A1 | 11/2009 | Klip et al. |
| 2009/0298665 A1 | 12/2009 | Dolecek et al. |
| 2009/0317305 A1 | 12/2009 | Hudock et al. |
| 2010/0026986 A1 | 2/2010 | Stanton et al. |
| 2010/0042037 A1 | 2/2010 | Felt et al. |
| 2010/0081196 A1 | 4/2010 | Felt et al. |
| 2010/0210441 A1 | 8/2010 | Dolecek |
| 2010/0267538 A1 | 10/2010 | Green et al. |
| 2010/0273627 A1 | 10/2010 | Hudock et al. |
| 2011/0003675 A1 | 1/2011 | Dolecek |
| 2011/0028295 A1 | 2/2011 | Menhennett et al. |
| 2011/0059834 A1 | 3/2011 | Eberle |
| 2011/0077140 A1 | 3/2011 | Holmes et al. |
| 2011/0086752 A1 | 4/2011 | Brierton |
| 2011/0100919 A1 | 5/2011 | Dorian et al. |
| 2011/0136646 A1 | 6/2011 | Pearce et al. |
| 2011/0136650 A1 | 6/2011 | Ellingboe et al. |
| 2011/0152055 A1 | 6/2011 | Pittinger et al. |
| 2011/0178453 A1 | 7/2011 | Pages et al. |
| 2011/0224064 A1 | 9/2011 | Pittinger et al. |
| 2014/0045671 A1 | 2/2014 | Min et al. |

FOREIGN PATENT DOCUMENTS

| | | |
|---|---|---|
| WO | WO 9911305 A1 | 3/1999 |
| WO | WO 0054823 A1 | 9/2000 |
| WO | WO 0124848 A1 | 4/2001 |
| WO | WO 0166172 A2 | 9/2001 |
| WO | WO 2005003738 A2 | 9/2001 |
| WO | WO 2006071496 A2 | 7/2006 |
| WO | WO 2007143386 A2 | 12/2007 |
| WO | WO 2008140561 A1 | 11/2008 |
| WO | WO 2008156906 A1 | 12/2008 |
| WO | WO 2010014330 A2 | 2/2010 |
| WO | WO 2010019317 A2 | 2/2010 |
| WO | WO 2010019318 A1 | 2/2010 |
| WO | WO 2010030406 A1 | 3/2010 |

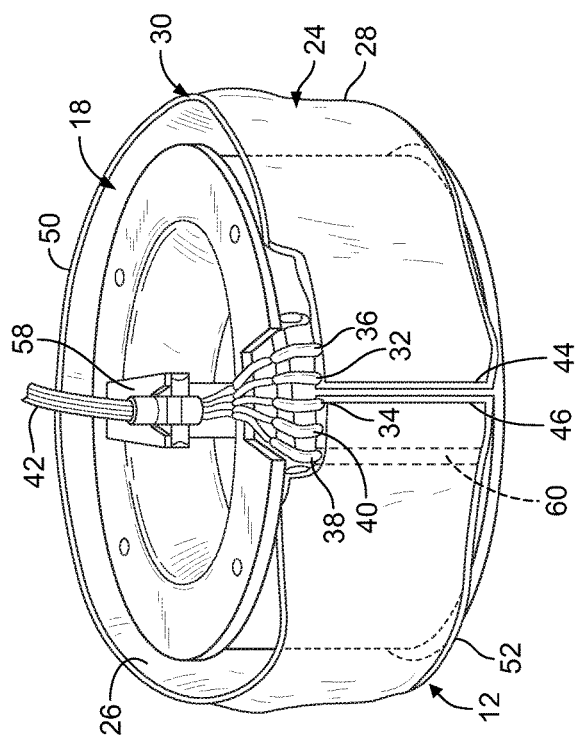
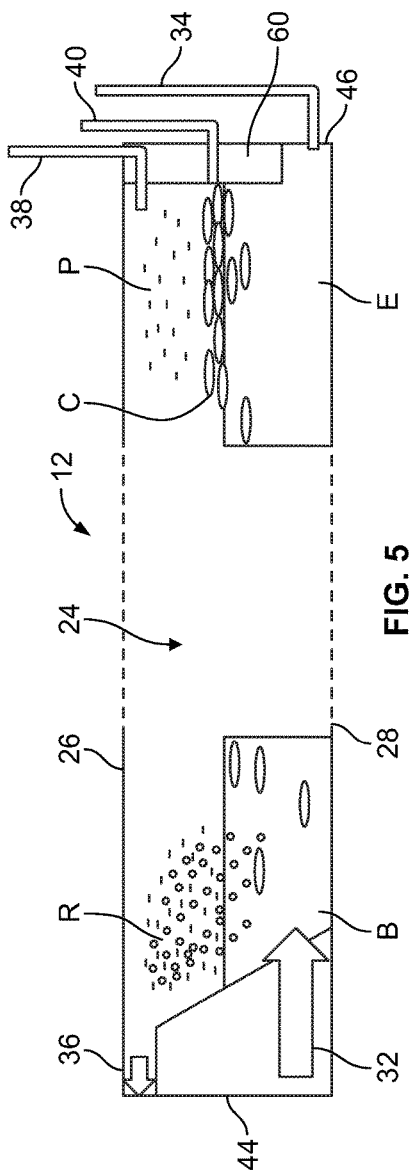
FIG. 4
FIG. 5

FIVE-PORT BLOOD SEPARATION CHAMBER AND METHODS OF USING THE SAME

CROSS REFERENCE TO RELATED APPLICATIONS

This application claims the benefit of and priority of U.S. Provisional Patent Application Ser. No. 62/198,369, filed Jul. 29, 2015, the contents of which are incorporated by reference herein.

BACKGROUND

Field of the Disclosure

The present disclosure relates to blood separation systems and methods. More particularly, the present disclosure relates to single-stage blood separation chambers and methods for separating blood in such chambers.

Description of Related Art

Various blood processing systems now make it possible to collect particular blood constituents, rather than whole blood, from donors. Typically, in such systems, whole blood is drawn from a donor, the particular blood component or constituent is removed and collected, and the remaining blood constituents are returned to the donor. By thus removing only particular constituents, potentially less time is needed for the donor's body to return to normal, and donations can be made at more frequent intervals than when whole blood is collected. This increases the overall supply of blood constituents, such as plasma and platelets, made available for health care.

Such systems may also be used for non-donation processing of a patient's blood. For example, whole blood may be drawn from a patient, with one component being removed and discarded (rather than being collected for donation). The remaining blood components may then be returned to the patient, along with a replacement fluid, if necessary. In other procedures in which the blood of a patient is being processed, at least one of the separated components may be collected, rather than all of the components being either returned to the patient or discarded.

Whole blood is typically separated into its constituents through centrifugation. This requires that the whole blood be passed through a centrifuge after it is withdrawn from, and before it is returned to, the donor or patient. To avoid contamination and possible infection of the donor, the blood is typically contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded. Exemplary centrifuges and disposable processing assemblies are shown and described in U.S. Pat. Nos. 6,254,784 and 6,312,607, both of which are incorporated herein by reference.

As the whole blood is spun by the centrifuge, the heavier (greater specific gravity) components, such as red blood cells, move radially outwardly away from the center of rotation toward the outer or "high-G" wall of a separation chamber included as part of the fluid processing assembly. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber of the fluid processing assembly. For example, therapeutic plasma exchange involves separating plasma from cellular blood components, collecting and disposing of the plasma, and returning the cellular blood components and a replacement fluid to the patient.

One possible disadvantage of known blood separation chambers is that they are typically suitable for only one type of blood separation procedure, thereby requiring the use of a different disposable processing assembly depending on the components into which the blood is to be separated. Accordingly, the need remains for a blood separation chamber that is capable of being used in a variety of different blood separation procedures.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a blood separation chamber is provided with a single stage. The single stage is defined by inner and outer walls, which are joined along at least a portion of their perimeters. A blood inlet port, red blood cell outlet port, platelet-rich plasma outlet port, platelet-poor plasma outlet port, and buffy coat outlet port are connected to the single stage.

In another aspect, a blood separation method is provided in which blood is flowed into the single stage of a blood separation chamber. The blood is separated in the single stage into at least first and second separated blood components. At least a portion of the first separated blood component is flowed out of the single stage by a first outlet port. At least a portion of the second separated blood component is flowed out of the single stage by a second outlet port. Flow out of the single stage by third and fourth outlet ports is prevented.

In yet another aspect, a blood separation method is provided in which blood is flowed into the single stage of a blood separation chamber. The blood is separated in the single stage into first, second, and third separated blood components. At least a portion of the first separated blood component is flowed out of the single stage by a first outlet port. At least a portion of the second separated blood component is flowed out of the single stage by a second outlet port. At least a portion of the third separated blood component is flowed out of the single stage by a third outlet port. Flow out of the single stage by a fourth outlet port is prevented.

In another aspect, a blood separation method is provided in which blood is flowed into the single stage of a blood separation chamber including a blood inlet port and four outlet ports. The blood is separated in the single stage into a plurality of separated blood components. At least a portion of at least one of the separated blood components is flowed out of the single stage with the four outlet ports in a first flow configuration in which at least one of the outlet ports is open to fluid flow and at least one of the other outlet ports is closed to fluid flow. The four outlet ports are moved to a second flow configuration in which at least one outlet port which is open to fluid flow in the first flow configuration is closed to fluid flow and/or at least one outlet port which is closed to fluid flow in the first flow configuration is open to fluid flow. At least a portion of at least one of the separated blood components is flowed out of the single stage with the four outlet ports in the second flow configuration.

BRIEF DESCRIPTION OF THE DRAWINGS

FIG. 4 is a top perspective view of the spool of the blood processing system of FIG. 1 in its upright position and carrying a blood separation chamber that is configured according to an aspect of the present disclosure;

FIG. 5 is a schematic diagram of the blood separation chamber of FIG. 4;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
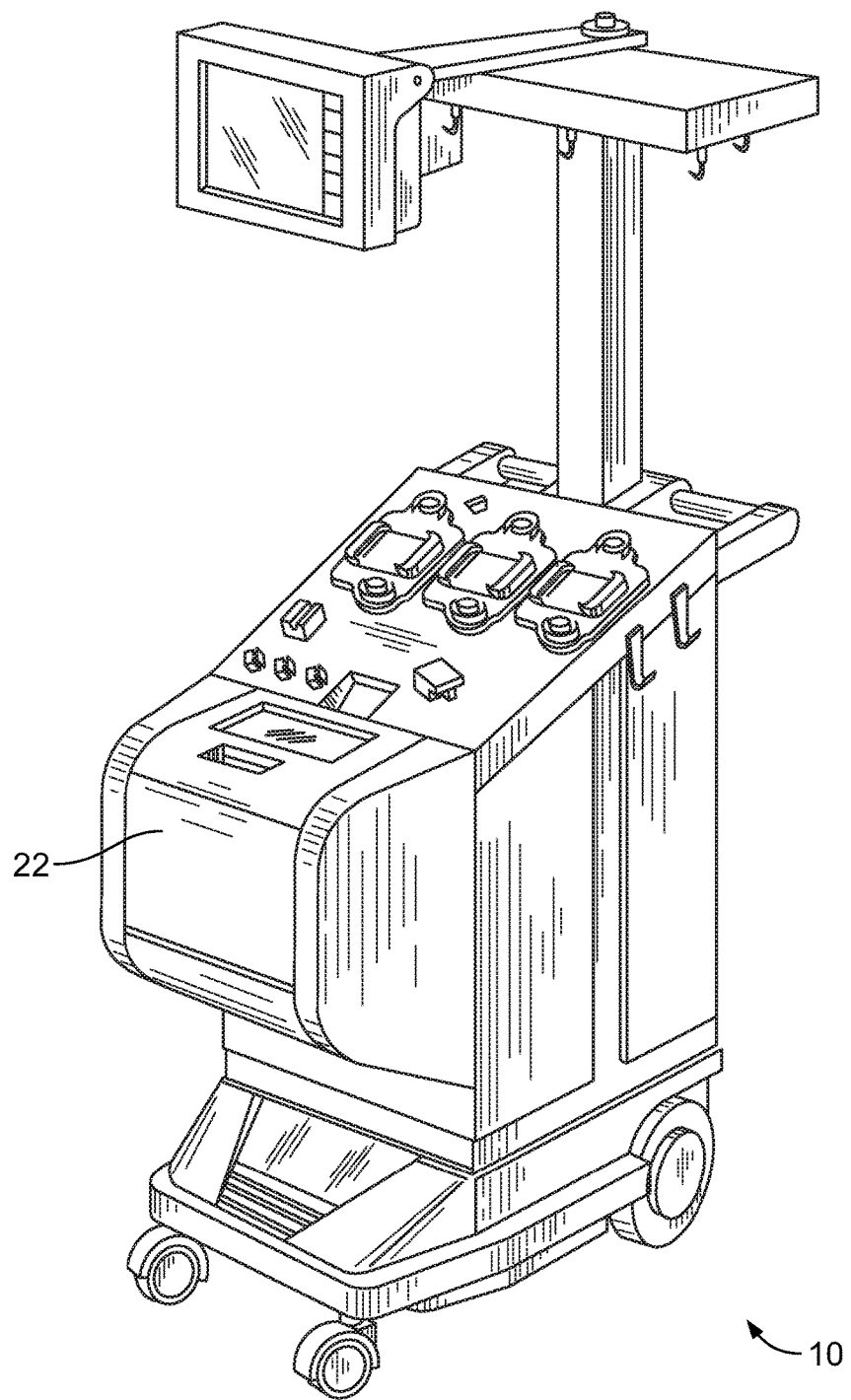
FIG. 1 is a perspective view of an exemplary blood processing system that may be used in combination with a blood separation chamber according to the present disclosure.
Figure 2:
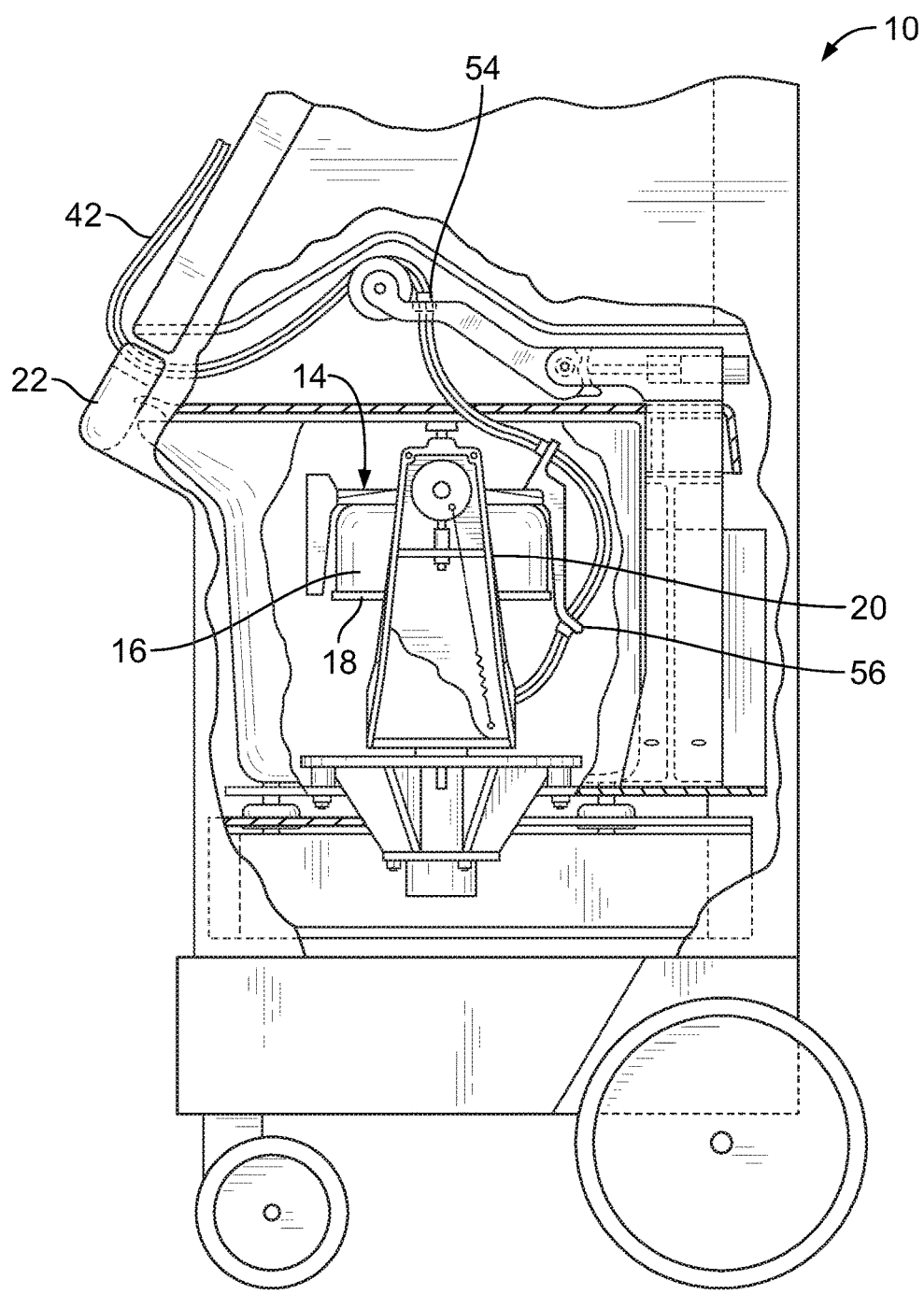
FIG. 2 is a side elevational view, with portions broken away and in section, of the blood processing system of FIG. 1, with a centrifuge bowl and spool of the system being shown in their operating position.
Figure 3:
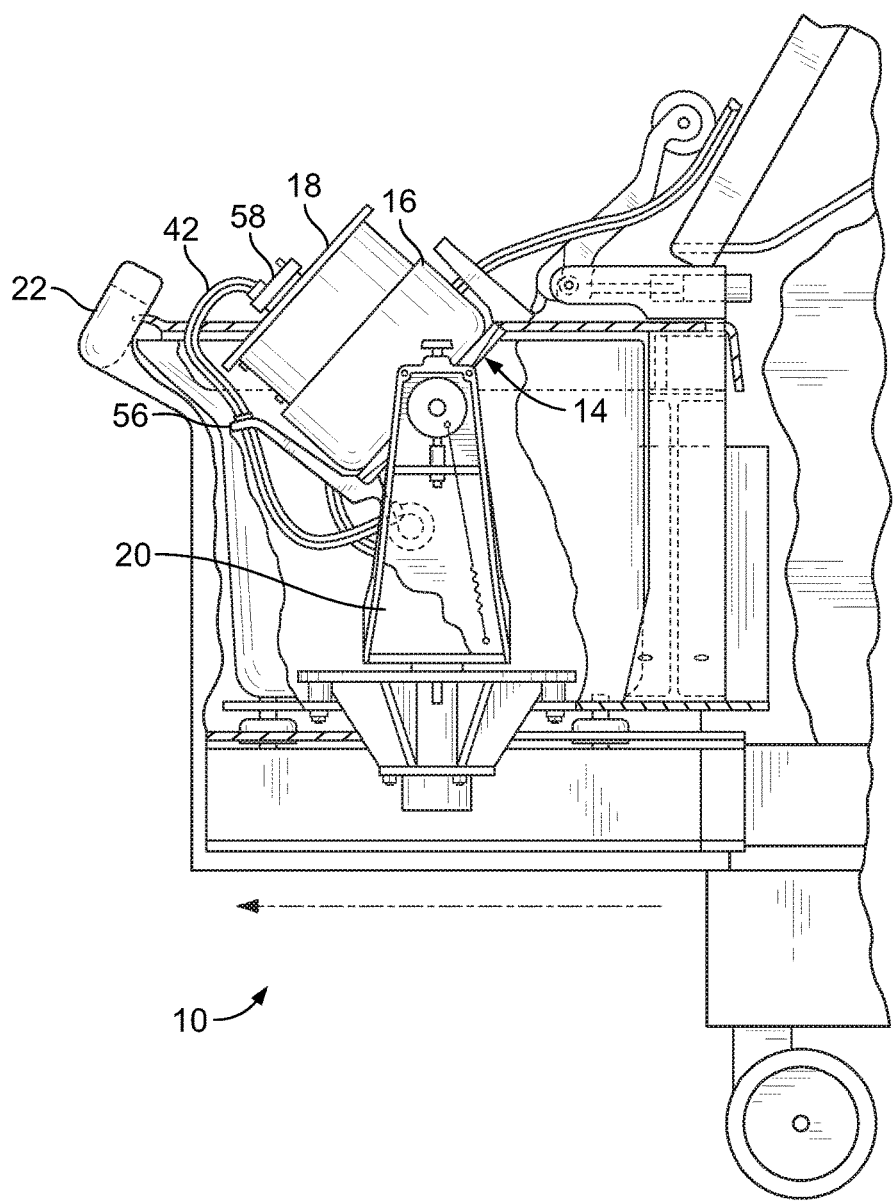
FIG. 3 is a side elevational view, with portions broken away and in section, of the blood processing system of FIG. 1, with the centrifuge bowl and spool shown in an upright position for receiving a blood separation chamber.

FIGS. 1-3 show an exemplary blood processing system 10 that is suitable for use with blood separation chambers according to aspects of the present disclosure. The blood processing system 10 may be provided generally according to known design, such as the system currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696 or U.S. Patent Application Publication No. 2014/0045671, both of which are hereby incorporated herein by reference.

While blood separation chambers will be primarily described herein as being used in combination with a blood processing system 10 of the type shown in FIGS. 1-3, it should be understood that blood separation chambers according to the present disclosure may be employed in combination with differently configured blood processing systems without departing from the scope of the present disclosure. In particular, the blood processing system 10 of FIGS. 1-3 is configured for use in combination with a blood separation chamber having flexible walls, but it should be understood that blood separation chambers according to the present disclosure may be provided with substantially rigid walls, in which case a differently configured blood processing system (i.e., one particularly configured for use with a rigid blood separation chamber) may be advantageous. As will be described in greater detail, it is also within the scope of the present disclosure for the blood processing system 10 to be used in combination with a blood separation chamber having walls with at least one section formed of a substantially flexible material and at least one section formed of a substantially rigid material.

The blood processing system 10 is used in combination with a single-use flow circuit to form a centrifugation system. In one embodiment, the flow circuit may be similar in form to the flow circuit described in U.S. Patent Application Publication No. 2014/0045671, which includes a variety of components fluidly connected by tubing. The flow circuit may include any number of different components, such as a blood access device (e.g., a needle used to access blood from a blood source, such as a living donor, or a non-living source, such as a blood bag), one or more pump devices that may interact with corresponding components (e.g., tubing loops that are engaged by peristaltic pumps) of the blood processing system 10 to pump fluid through the flow circuit, and a blood separation chamber 12 (FIGS. 4 and 5). It may be advantageous for the flow circuit to be provided as a disposable or single-use item, while the blood processing system 10 is provided as a durable device that may be used repeatedly with matching flow circuits.

A. The Blood Processing System and Centrifuge

The system 10 includes a centrifuge 14 used to centrifugally separate blood components. The system 10 may be programmed to separate blood into a variety of components (e.g., platelet-rich plasma and red blood cells or platelet-poor plasma, red blood cells, and buffy coat). According to an aspect of the present disclosure, which will be described in greater detail, the blood separation chamber 12 is configured for use in combination with a variety of different blood separation procedures.

The illustrated centrifuge 14 is of the type shown in U.S. Pat. No. 5,316,667, which is incorporated herein by reference. The centrifuge 14 comprises a bowl 16 and a spool 18. The bowl 16 and spool 18 are pivoted on a yoke 20 between an operating position (FIG. 2) and a loading/unloading position (FIG. 3). The centrifuge 14 is illustrated as being housed within the interior of the blood processing system 10, in which case a door 22 may be provided to allow access to the centrifuge 14 for loading and unloading the blood separation chamber 12. The door 22 remains closed during operation to protect and enclose the centrifuge 14.

When in the loading/unloading position, the spool 18 can be accessed by movement at least partially out of the bowl 16, as FIG. 3 shows. In this position, the operator installs a flexible or partially rigid and partially flexible blood separation chamber 12 (see FIG. 4) onto the spool 18. Closure of the spool 18 and bowl 16 encloses the chamber 12 for processing. When closed, the spool 18 and bowl 16 are pivoted into the operating position of FIG. 2 for rotation of the chamber 12 about an axis, as will be described in greater detail.

B. The Blood Separation Chamber

The blood separation chamber 12 is provided as a single-stage device. This is in contrast to a multi-stage separation device, in which blood is separated into two or more components in a first stage, with one of the separated components thereafter being flowed into a second stage of the device for further fractionation. In a single-stage device, it is intended that blood is separated into its final separated components in a single stage of the device, rather than flowing a portion or fraction of the blood out of the single stage for further separation or fractionation. By way of example, the first stage of a known two-stage blood separation chamber suitable for use with the system 10 of FIGS. 1-3 wraps around only a portion of the outer surface of the spool 18 (with the second stage of the chamber wrapping around the remainder of the outer surface of the spool 18), providing a separation area of approximately 130 $cm^2$. In contrast, the chamber 12 of FIG. 4 (with a single stage 24 that wraps around substantially the entire outer surface of the spool 18) may provide a separation area of approximately 230 $cm^2$, although it is also within the scope of the present disclosure for the separation area to be some other size, such as a smaller size that wraps the single stage 24 around only a portion of the outer surface of the spool 18. While a single-stage chamber 12 according to the present disclosure is intended to provide all of the required separation functionality, it should be understood that use of a single-stage chamber 12 is not limited to any particular blood separation procedure and that a blood component separated within the single stage 24 of the chamber 12 may be further processed (e.g., by being passed through a leukocyte reduction filter or adsorption column or being subjected to light inactivation) without departing from the scope of the present disclosure.

The blood separation chamber 12 is defined by an inner wall 26 and an outer wall 28 (FIG. 5). The walls are referred to as "inner" and "outer" in reference to their relative positions to the axis of rotation of the centrifuge 14 when the chamber 12 is mounted onto the spool 18. The inner and outer walls 26 and 28 are joined together along at least a portion of their perimeters at a perimeter seal 30 (FIG. 4) to define a single stage 24 between the walls 26 and 28. By way of example, the walls 26 and 28 may be joined by thermal bonding or by using an adhesive. In the illustrated embodiment, a portion of the walls 26 and 28 is formed of a flexible material, which allows the chamber 12 to be wrapped around the spool 18, as shown in FIG. 4. Another portion of the walls 26 and 28 is formed of a rigid material (e.g., a rigid plastic material) to define contours that affect the flow of blood and blood components within the blood separation chamber 12. The region of the blood separation chamber 12 into which blood is introduced (illustrated in FIGS. 5 and 6B as the left end of the blood separation chamber 12 and illustrated in FIG. 6A as the right end) may be formed of a flexible material, while the opposite end of the blood separation chamber 12 (illustrated in FIGS. 5 and 6B as the right end of the blood separation chamber 12 and illustrated in FIG. 6A as the left end) may be formed of a rigid material.

In another embodiment, the inner and outer walls 26 and 28 are substantially entirely formed of a flexible material. In yet another embodiment, the inner and outer walls may be formed of a substantially rigid material (which allows for the chamber to be a molded structure), in which case an alternative centrifuge configuration may be appropriate for engaging and rotating the chamber. It is also within the scope of the present disclosure for different portions of one or both of the walls of the chamber to be formed of flexible and rigid materials than the arrangement of the flexible and rigid portions employed in the illustrated embodiment.

As FIGS. 4, 5, 6A, and 6B illustrate, there are five ports 32, 34, 36, 38 and 40 connected to the single stage 24. The ports are referred to herein as the blood inlet port 32, the red blood cell outlet port 34, the platelet-rich plasma outlet port 36, the platelet-poor plasma outlet port 38, and the buffy coat outlet port 40. The ports 32, 34, 36, 38, and 40 may be variously configured without departing from the scope of the present disclosure. In one embodiment, each port is formed of a rigid or semi-rigid material and arranged in a generally tubular configuration for connection to tubing of the flow circuit that is gathered into an umbilicus 42 (FIGS. 2-4). In other embodiments, the individual ports may be differently configured from each other and differently configured from what is shown in FIGS. 4, 5, 6A, and 6B. One or more of the tubes associated with the ports and/or one or more of the ports themselves may be provided with an associated flow control device (e.g., a clamp or valve) that may be actuated by a controller of the system 10 (e.g., a microprocessor) to selectively allow and prevent fluid flow through the tubing or port, as will be described herein.

In addition to a flow control device, one or more of the tubes associated with the ports (or a tube or flow conduit in fluid communication with such a tube) may be acted upon by a pump to actively draw fluid into the chamber 12 (in the case of an inlet port) or out of the chamber 12 (in the case of an outlet port) via the tube. For example, in one embodiment, separate pumps act upon the tubes associated with each of the blood inlet port 32, the platelet-rich plasma outlet port 36, the platelet-poor plasma outlet port 38, and the buffy coat outlet port 40. While there is no pump acting upon the tube associated with the red blood cell outlet port 34 in this exemplary embodiment, it is also within the scope of the present disclosure for a different port to be provided without an associated pump. If fluid flow through one of the tubes associated with the ports is not directly controlled by an associated pump, as in the case of the red blood cell outlet port 34 in the exemplary embodiment, or if the pump associated with one of the tubes is made inactive (and flow through the tube is not prevented by a flow control device), then flow therethrough is dependent upon the operation of the pumps controlling fluid flow through the other tubes under conservation of mass principles (i.e., the flow rate through such a tube is equal to the difference between the rate at which fluid is pumped into the chamber 12 and the flow rate at which fluid is pumped out of the chamber 12 through the other ports). In another embodiment, the system 10 includes at least five pumps, with a different pump corresponding to each tube associated with a port (or a tube or flow conduit in fluid communication with such a tube), which may allow for improved control over flow into and out of the chamber 12. If fluid is to flow through a tube, the associated pump may be actuated to directly control such flow; otherwise, as described above and as appropriate, the pump may be inactive to allow fluid to flow through the tube under conservation of mass principles. A pump may also be inactive when there is to be no fluid flow through the associated tube, in which case a flow control device associated with the tube may also be actuated to physically close the tube to prevent fluid flow therethrough.

Figure 6A:
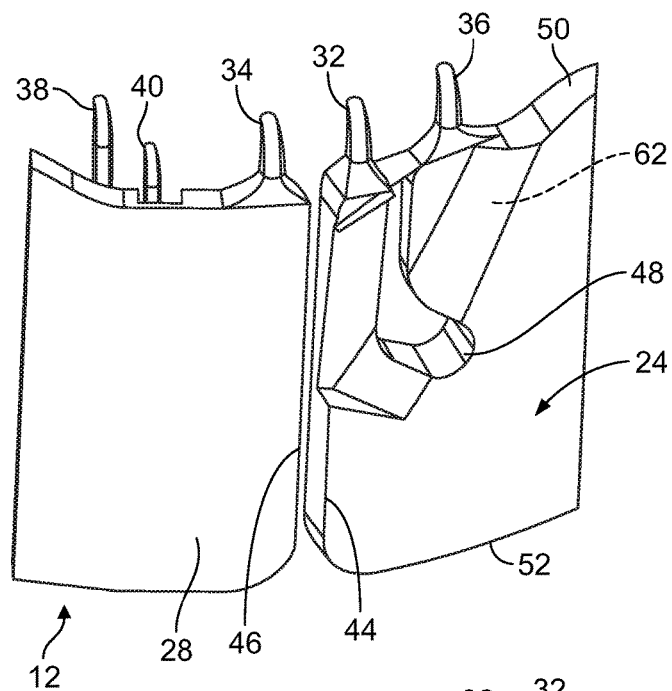
FIG. 6A is top perspective view of a portion of the blood separation chamber of FIG. 4 when mounted on the spool of the blood processing system of FIG. 1, as viewed from a radially outward position.
Figure 6B:
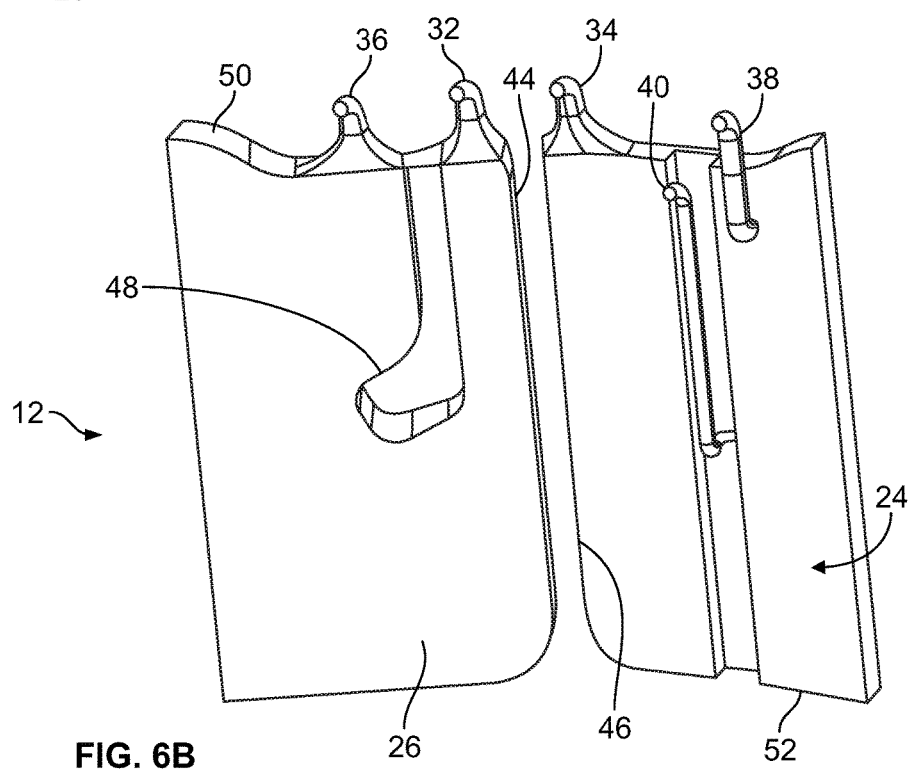
FIG. 6B is a top perspective view of the portion of the blood separation chamber of FIG. 6A, as viewed from a radially inward position.

The inner and outer walls 26 and 28 have lateral edges 44 and 46, with the first lateral edges 44 of the inner and outer walls 26 and 28 being at least partially joined together and the second lateral edges 46 of the walls 26 and 28 being at least partially joined together to define the single stage 24. In the illustrated embodiment, the blood inlet port 32 and the platelet-rich plasma outlet port 36 are connected to the single stage 24 adjacent to the first lateral edge 44, while the other three ports 34, 38, and 40 are connected to the single stage 24 adjacent to the second lateral edge 46 (FIG. 5). FIGS. 4, 6A, and 6B show the edges 44 and 46 positioned adjacent to each other when the chamber 12 is mounted onto the spool 18, but it should be understood that fluid entering into any of the ports 34, 38, and 40 adjacent to the second lateral edge 46 must traverse substantially the entire length of the single stage 24 (as best shown in FIG. 5), traveling around substantially the entire outer surface of the spool 18 from a position at or adjacent to the first lateral edge 44 (i.e., the blood inlet port 32) to a position at or adjacent to the second lateral edge 46 (i.e., the corresponding outlet port 34, 38, 40).

The chamber 12 of FIGS. 4 and 5 is illustrated as a belt or band that includes two lateral edges 44 and 46 and may be wrapped around the spool 18, but it is also within the scope of the present disclosure for the chamber to define a complete loop or annulus. If the chamber is so configured, then it may be slid or otherwise axially advanced onto the spool 18, rather than being wrapped around the spool 18. If the chamber is provided as a complete loop or annulus, it may be advantageous for the chamber to include one complete interior wall or seal that acts as a terminus. Such a terminus allows for fluid flow from one side of the terminus (which effectively provides a first lateral edge) to the other side of the terminus (which effectively provides a second lateral edge), while preventing fluid from flowing completely around the chamber, thereby mimicking the flow boundaries created by the illustrated belt- or band-shaped chamber 12.

The single stage 24 may further include one or more partial interior walls or seals, which are locations within the single stage 24 at which the inner and outer walls 26 and 28 are joined together. If provided, these interior seals alter the way in which blood and/or separated blood components move through the single stage 24. In the illustrated embodiment, the single stage 24 may include an interior seal 48 (FIGS. 6A and 6B) that is positioned between the blood inlet port 32 and the platelet-rich plasma outlet port 36. If provided, such an interior seal 48 prevents blood entering into the single stage 24 from immediately flowing into the platelet-rich plasma outlet port 36. Instead, the interior seal 48 forces the blood to move to a location more spaced away from the platelet-rich plasma outlet port 36, which allows the blood to separate into its components, with those components moving toward the appropriate outlet port.

In addition to the lateral edges 44 and 46, the inner and outer walls 26 and 28 may also include first and second axial edges 50 and 52, with the first axial edges 50 of the inner and outer walls 26 and 28 being at least partially joined together and the second axial edges 52 of the walls 26 and 28 being at least partially joined together to define the single stage 24. FIG. 6B shows three of the ports 32, 34, and 36 extending through the perimeter seal 30 at the first axial edge 50 to access the single stage 24, while the other two ports 38 and 40 open into the single stage 24 at a location between the axial edges 50 and 52. In particular, the platelet-poor plasma outlet port 38 and the buffy coat outlet port 40 extend through the inner wall 26 to access the single stage 24 in the illustrated embodiment. In other embodiments, the individual ports may be connected to and/or open into the single stage 24 at different locations without departing from the scope of the present disclosure.

C. Blood Separation

As described above, the chamber 12 may be used in a variety of blood separation procedures. For any of these procedures, blood B (which may include an amount of anticoagulant or other non-bodily fluid) is flowed into the single stage 24 of the chamber 12 by one of the ports (typically the blood inlet port 32). The centrifuge 14 rotates the chamber 14 (positioned between the bowl 16 and spool 18) about an axis to separate the blood within the single stage 24 into two or more components, depending on their density. The separated components that are relatively dense move toward the outer wall 28 (i.e., toward the bowl 16), while the separated components that are less dense move toward the inner wall 26 (i.e., toward the spool 18).

The low density component may be a platelet-rich plasma layer R (FIG. 5), which is comprised substantially of plasma and platelets, but may include amounts of other materials (e.g., anticoagulant and lower density leukocytes) without departing from the scope of the present disclosure. Another possible low density component is a platelet-poor plasma layer P (FIG. 5), which is comprised substantially of cell-free plasma, but may include amounts of other materials (e.g., anticoagulant) without departing from the scope of the present disclosure. The two low density layers R and P may coexist in the chamber 12, as shown in FIG. 5, with the principal difference between the two layers R and P being the platelets from the separated blood that settle into the platelet-rich plasma layer R.

The high density component may be a red blood cell layer E (FIG. 5), which is comprised substantially of packed red blood cells, but may include amounts of other materials (e.g., higher density leukocytes) without departing from the scope of the present disclosure.

An intermediate density component may also be separated from the low and high density components. The intermediate density component may be a buffy coat layer C (FIG. 5), which is comprised substantially of platelets and white blood cells, but may include amounts of other materials without departing from the scope of the present disclosure.

In the illustrated embodiment, the centrifuge 14 rotates the chamber 12 about the rotational axis using the umbilicus 42 defined by the gathered tubing associated with the ports 32, 34, 36, 38, and 40, which connects the chamber 12 to the other components of the flow circuit (which are typically positioned outside of the centrifuge 14). As FIG. 2 shows, a non-rotating (zero omega) holder 54 holds an upper portion of the umbilicus 42 in a non-rotating position above the spool 18 and bowl 16. A holder 56 on the yoke 20 rotates a mid-portion of the umbilicus 42 at a first (one omega) speed about the suspended spool 18 and bowl 16. Another holder 58 (FIGS. 3 and 4) rotates a lower end of the umbilicus 42 at a second speed twice the one omega speed (the two omega speed), at which two omega speed the umbilicus 42 drives the rotation of the spool 18 and bowl 16.

The outlet port or ports configured to receive the more dense separated component or components (e.g., layer E) may open into the single stage 24 at or adjacent to the outer wall 28 of the chamber 12 (i.e., at a radially outward position). In the illustrated embodiment, the red blood cell outlet port 34 may be located at a radially outward position (as in FIG. 5) to receive separated red blood cells, which are more dense than other separated blood components.

The outlet port or ports configured to receive the less dense separated component or components (e.g., layers R and P) may open into the single stage 24 at or adjacent to the inner wall 26 of the chamber 12 (i.e., at a radially inward position). In the illustrated embodiment, the platelet-poor plasma outlet port 38 and the platelet-rich plasma outlet port 36 may be located at a radially inward position (as in FIG. 5) to receive separated plasma (either containing platelets or being substantially cell-free), which is less dense than other separated blood components (e.g., packed red blood cells).

The outlet port or ports configured to receive a separated blood component or components of intermediate density (e.g., layer C) may open into the single stage 24 at radially intermediate position (e.g., at a location that is farther from the axis of rotation than the plasma outlet ports 36 and 38, but closer to the axis of rotation than the red blood cell outlet port 34), which may be approximately midway between the inner and outer walls 26 and 28 in one embodiment. In the illustrated embodiment, the buffy coat outlet port 40 may be located at a radially intermediate position (as in FIG. 5) to receive separated buffy coat (substantially comprised of platelets and white blood cells), which is more dense than cell-free plasma and less dense than red blood cells, as described above.

According to one possible approach to positioning the buffy coat outlet port 40 at a radially intermediate position, the portion of the chamber 12 adjacent to the second lateral edge 46 may be formed of a rigid material (as described above), which may define a red blood cell barrier 60 (FIGS. 4 and 5). The red blood cell barrier 60 extends radially outwardly from the inner wall 26 of the chamber 12 toward the outer wall 28 without contacting the outer wall 28. By such a configuration, the red blood cell barrier 60 allows only separated blood components positioned adjacent to the outer wall 28 (i.e., separated red blood cells) to move to the red blood cell outlet port 34, with the less dense components being prevented from flowing to the red blood cell outlet port 34 by the barrier 60.

In the illustrated embodiment, the buffy coat outlet port 40 is connected to the single stage 24 at a location that is positioned at the barrier 60. As can be seen in FIG. 5, the buffy coat outlet port 40 may be configured to open into the single stage 24 at an upstream surface of the barrier 60, such that buffy coat moving into contact with the barrier 60 at a radially intermediate position within the single stage 24 flows into the buffy coat outlet port 40. Other approaches to positioning a port at a radially intermediate position within the single stage 24 may also be employed without departing from the scope of the present disclosure. For example, if the portion of the chamber 12 adjacent to the second lateral edge 46 is formed of a flexible material, the red blood cell barrier 60 may comprise a formation on the outer surface of the spool 18, which influences the shape assumed by that portion of the chamber 12 and the position of the buffy coat outlet port 40 (as shown in FIG. 6B) when the chamber 12 is positioned between the spool 18 and the bowl 16.

As for the blood inlet port 32, it is shown in FIG. 5 as opening into the single stage 24 at or adjacent to the outer wall 28 (i.e., at a radially outward position), but it is also within the scope of the present disclosure for the blood inlet port 32 to open into the single stage 24 at a different radial position.

1. First Exemplary Procedure

Depending on the nature of the procedure, one or more of the outlet ports may be closed at any time during the procedure to prevent fluid from exiting the single stage 24 therefrom. In one exemplary procedure, the platelet-poor plasma outlet port 38 and the buffy coat outlet port 40 may be closed (e.g., by actuation of a valve or clamp or comparable fluid flow control device associated with the port or the tubing connected to the port) to prevent fluid flow therethrough. Before or after installing the flow circuit onto the system 10, an operator may input (using a touchscreen or associated computer terminal or other data entry device) the blood separation procedure to be carried out by the system 10. Upon receiving this information, the system controller may cause the fluid flow control devices associated with the platelet-poor plasma outlet port 38 and the buffy coat outlet port 40 (or the tubing connected to the ports) to move from an open condition to a closed condition or to remain in a closed condition during the separation procedure.

With fluid flow being restricted to only the appropriate inlet and outlet ports, a separation procedure may be carried out by the system 10 to separate blood into the various components, with the red blood cell layer E moving under the influence of centrifugal force toward the outer wall 28 of the chamber 12 (as illustrated in the right side of FIG. 5) and the platelet-rich plasma layer R moving under the influence of centrifugal force toward the inner wall 26 of the chamber 12 (as illustrated in the left side of FIG. 5). The buffy coat layer C may move to a radially intermediate position between the inner and outer walls 26 and 28, while the platelet-poor plasma layer P moves under the influence of centrifugal force toward the inner wall 26 (as illustrated in the right side of FIG. 5).

At least a portion of the red blood cell layer E moves from one lateral edge 44 of the single stage 24 toward the other lateral edge 46 (around the outer surface of the spool 18), where it enters into the red blood cell outlet port 46. At least a portion of the platelet-rich plasma layer R moves around the interior seal 48 (if present) and into the platelet-rich plasma outlet port 36, which is positioned adjacent to the same lateral edge 44 as the blood inlet port 32. Thus, it will be seen that (when the chamber 12 is configured as shown in FIGS. 4-6B) at least a portion of the platelet-rich plasma layer R may exit the single stage 24 without having to traverse all or substantially all of the length of the single stage 24, unlike the red blood cell layer E. However, it should also be understood that a portion of the platelet-rich plasma layer R (e.g., platelets settling into the platelet-rich plasma layer R from the buffy coat layer C) may traverse a greater portion of the single stage 24 before reaching the platelet-rich plasma outlet port 36.

The separated components may be flowed from the associated outlet port to any of a number of locations, including being flowed to a storage container or to a waste container or to a processing device (e.g., a filter) or to the blood source. In an exemplary red blood cell exchange procedure, the platelet-rich plasma layer R may be flowed from the platelet-rich plasma outlet port 36 (e.g., by operation of a platelet-rich plasma pump acting upon tubing connected to the platelet-rich plasma outlet port 36) to the blood source while the red blood cell layer E is flowed to a waste container. The platelets and plasma may be supplemented by a replacement fluid and/or red blood cells previously collected from a donor before being returned to the blood source, or replacement fluid and/or donated red blood cells may be separately conveyed to the blood source. This may be advantageous compared to typical red blood cell exchange procedures in which platelets may be separated with the red blood cells and discarded, rather than the platelets being returned to the blood source.

While platelet-rich plasma and red blood cell layers R and E may be of primary interest of this procedure, it is also within the scope of the present disclosure for the ports 38 and 40 associated with the platelet-poor plasma and buffy coat layers P and C to be selectively opened during the procedure. For example, if the system 10 determines that the buffy coat layer C is not properly positioned within the chamber 12 (as will be described), then the platelet-poor plasma outlet port 38 may be temporarily opened to adjust the position of the buffy coat layer C within the chamber 12. In the aforementioned exemplary red blood cell exchange procedure, the buffy coat outlet port 40 may be selectively opened to allow mononuclear cells to exit the chamber 12 via the buffy coat outlet port 40 and be returned to the blood source, rather than being discarded with the red blood cell layer E.

Similarly, it is also within the scope of the present disclosure for the red blood cell and platelet-rich plasma outlet ports 34 and 36 to be temporarily closed and/or for the flow rate therethrough to be temporarily adjusted during the procedure, which may be advantageous for adjusting the way in which the various components flow through the chamber 12. For example, rather than opening the platelet-poor plasma outlet port 38 to adjust the position of the buffy coat layer C within the chamber 12, the platelet-poor plasma outlet port 38 may remain closed while the rate of flow through the open platelet-rich plasma outlet port 36 is adjusted (e.g., by adjusting the operation of a platelet-rich plasma pump acting upon tubing connected to the platelet-rich plasma outlet port 36) to adjust the position of the buffy coat layer C within the chamber 12.

2. Second Exemplary Procedure

According to another exemplary procedure, the platelet-rich plasma outlet port 36 may be closed (e.g., by actuation of a valve or clamp or comparable fluid flow control device associated with the port or the tubing connected to the port) to prevent fluid flow therethrough. Before or after installing the flow circuit onto the system 10, an operator may input (using a touchscreen or associated computer terminal or other data entry device) the blood separation procedure to be carried out by the system 10. Upon receiving this information, the system controller may cause the fluid flow control device associated with the platelet-rich plasma outlet port 36 (or the tubing connected to the port) to move from an open condition to a closed condition or to remain in a closed condition during the separation procedure.

With fluid flow being restricted to only the appropriate inlet and outlet ports, a separation procedure may be carried out by the system 10 to separate blood into the various components, as described above with respect to the first exemplary procedure. At least a portion of the red blood cell layer E moves from one lateral edge 44 of the single stage 24 toward the other lateral edge 46 (around the outer surface of the spool 18), where it enters into the red blood cell outlet port 34 at a radially outward position. At least a portion of the platelet-poor plasma layer P also moves from the first lateral edge 44 of the single stage 24 toward the second lateral edge 46, where it enters into the platelet-poor plasma outlet port 38 at a radially inward position. At least a portion of the buffy coat layer C also moves from one lateral edge 44 of the single stage 24 toward the other lateral edge 46, where it enters into the buffy coat outlet port 40 at a radially intermediate position. Thus, it will be seen that the red blood cell layer E exits the chamber 12 at a position that is radially outward of the position at which the buffy coat layer C exits the chamber 12, which is radially outward of the position at which the platelet-poor plasma layer P exits the chamber 12.

The separated components may be flowed from the associated outlet port to any of a number of locations, including being flowed to a storage container or to a waste container or to a processing device (e.g., a filter) or to the blood source. In an exemplary platelet depletion procedure, the platelet-poor plasma and red blood cell layers P and E may be flowed from the platelet-poor plasma outlet port 38 and the red blood cell outlet port 34, respectively, to the blood source while the buffy coat layer C (including platelets) is flowed to a waste container. The red blood cells and plasma may be supplemented by a replacement fluid before being returned to the blood source, or replacement fluid may be separately conveyed to the blood source. This may be advantageous compared to platelet depletion procedures in which platelets are accumulated in the second stage of a multiple stage separation chamber. If the second stage becomes completely filled with platelets without the target volume of platelets being removed or the target volume of blood being processed, then the blood source/patient must go through the procedure a second time. In contrast, a chamber 12 according to the present disclosure may be operated to continuously remove platelets from the chamber 12 to a waste container, which may have a greater volume than the chamber 12, thereby allowing for the target amount of platelets to be removed or for the target amount of blood to be processed in a single procedure.

Additionally, it is also within the scope of the present disclosure for the platelet-rich plasma outlet port 36 to be selectively opened during the procedure. For example, if the system 10 determines that the buffy coat layer C is not properly positioned within the chamber 12 (as will be described), then the platelet-rich plasma outlet port 36 may be temporarily opened to adjust the position of the buffy coat layer C within the chamber 12. Furthermore, one or more of the other outlet ports 34, 38, and 40 may be temporarily closed and/or the flow rate therethrough may be temporarily adjusted during the procedure, which may be advantageous for adjusting the way in which the various components flow through the chamber 12. For example, rather than opening the platelet-rich plasma outlet port 36 to adjust the position of the buffy coat layer C within the chamber 12, the platelet-rich plasma outlet port 36 may remain closed while the rate of flow through the open platelet-poor plasma outlet port 38 is adjusted (e.g., by adjusting the operation of a platelet-poor plasma pump acting upon tubing connected to the platelet-poor plasma outlet port 38) to adjust the position of the buffy coat layer C within the chamber 12.

3. Third Exemplary Procedure

According to yet another exemplary procedure, the platelet-poor plasma outlet port 38 may be closed (e.g., by actuation of a valve or clamp or comparable fluid flow control device associated with the port or the tubing connected to the port) to prevent fluid flow therethrough. Before or after installing the flow circuit onto the system 10, an operator may input (using a touchscreen or associated computer terminal or other data entry device) the blood separation procedure to be carried out by the system 10. Upon receiving this information, the system controller may cause the fluid flow control device associated with the platelet-poor plasma outlet port 38 (or the tubing connected to the port) to move from an open condition to a closed condition or to remain in a closed condition during the separation procedure.

With fluid flow being restricted to only the appropriate inlet and outlet ports, a separation procedure may be carried out by the system 10 to separate blood into the various components, as described above with respect to the first exemplary procedure. At least a portion of the red blood cell layer E moves from one lateral edge 44 of the single stage 24 toward the other lateral edge 46 (around the outer surface of the spool 18), where it enters into the red blood cell outlet port 34 at a radially outward position. At least a portion of the platelet-rich plasma layer R moves around the interior seal 48 (if present) and into the platelet-rich plasma outlet port 36, which is positioned adjacent to the same lateral edge 44 as the blood inlet port 32. At least a portion of the buffy coat layer C (which, in this exemplary procedure includes leukocytes, while being substantially free of platelets) also moves from one lateral edge 44 of the single stage 24 toward the other lateral edge 46, where it enters into the buffy coat outlet port 40 at a radially intermediate position.

The separated components may be flowed from the associated outlet port to any of a number of locations, including being flowed to a storage container or to a waste container or to a processing device (e.g., a filter) or to the blood source. In an exemplary white blood cell depletion procedure, the platelet-rich plasma and red blood cell layers R and E may be flowed from the platelet-rich plasma outlet port 36 and the red blood cell outlet port 34, respectively, to the blood source while the buffy coat layer C (including leukocytes) is flowed to a waste container. The red blood cells and platelet-rich plasma may be supplemented by a replacement fluid before being returned to the blood source, or replacement fluid may be separately conveyed to the blood source. This may be advantageous compared to batch-type white blood cell depletion procedures, as continuous separation and removal of leukocytes allows the procedure to be completed relatively quickly and does not require platelets to be collected from the buffy coat, which can decrease the amount of platelets conveyed to the blood source. In a variation of such a white blood cell depletion procedure, the blood drawn from the blood source may be mixed with hydroxyethyl starch before being separated, which allows for separation and collection of granulocytes.

Additionally, it is also within the scope of the present disclosure for the platelet-poor plasma outlet port 38 to be selectively opened during the procedure. For example, if the system 10 determines that the buffy coat layer C is not properly positioned within the chamber 12 (as will be described), then the platelet-poor plasma outlet port 38 may be temporarily opened to adjust the position of the buffy coat layer C within the chamber 12. Furthermore, one or more of the other outlet ports 34, 36, and 40 may be temporarily closed and/or the flow rate therethrough may be temporarily adjusted during the procedure, which may be advantageous for adjusting the way in which the various components flow through the chamber 12. For example, rather than opening the platelet-poor plasma outlet port 38 to adjust the position of the buffy coat layer C within the chamber 12, the platelet-poor plasma outlet port 38 may remain closed while the rate of flow through the open platelet-rich plasma outlet port 36 is adjusted (e.g., by adjusting the operation of a platelet-rich plasma pump acting upon tubing connected to the platelet-rich plasma outlet port 36) to adjust the position of the buffy coat layer C within the chamber 12.

4. Fourth Exemplary Procedure

According to another exemplary procedure, the platelet-rich plasma outlet port 36 and the buffy coat outlet port 40 may be closed (e.g., by actuation of a valve or clamp or comparable fluid flow control device associated with the port or the tubing connected to the port) to prevent fluid flow therethrough. Before or after installing the flow circuit onto the system 10, an operator may input (using a touchscreen or associated computer terminal or other data entry device) the blood separation procedure to be carried out by the system 10. Upon receiving this information, the system controller may cause the fluid flow control device associated with the platelet-rich plasma outlet port 36 and the buffy coat outlet port 40 (or the tubing connected to the ports) to move from an open condition to a closed condition or to remain in a closed condition during the separation procedure.

With fluid flow being restricted to only the appropriate inlet and outlet ports, a separation procedure may be carried out by the system 10 to separate blood into the various components, as described above with respect to the first exemplary procedure. At least a portion of the red blood cell layer E moves from one lateral edge 44 of the single stage 24 toward the other lateral edge 46 (around the outer surface of the spool 18), where it enters into the red blood cell outlet port 34 at a radially outward position. At least a portion of the platelet-poor plasma layer P also moves from the first lateral edge 44 of the single stage 24 toward the second lateral edge 46, where it enters into the platelet-poor plasma outlet port 38 at a radially inward position.

The separated components may be flowed from the associated outlet port to any of a number of locations, including being flowed to a storage container or to a waste container or to a processing device (e.g., a filter) or to the blood source. In an exemplary plasma exchange procedure, the cellular blood components may be flowed from the red blood cell outlet port 34 (e.g., by operation of a red blood cell pump acting upon tubing connected to the red blood cell outlet port 34) to the blood source while the platelet-poor plasma layer P is flowed to a waste container. The cellular blood components may be supplemented by a replacement fluid and/or plasma from a donor before being returned to the blood source, or replacement fluid and/or donated plasma may be separately conveyed to the blood source.

Additionally, it is also within the scope of the present disclosure for the platelet-rich plasma outlet port 36 and/or the buffy coat outlet port 40 to be selectively opened during the procedure. For example, if the system 10 determines that the buffy coat layer C is not properly positioned within the chamber 12 (as will be described), then the platelet-rich plasma outlet port 36 may be temporarily opened to adjust the position of the buffy coat layer C within the chamber 12. Furthermore, one or more of the other outlet ports 34 and 38 may be temporarily closed and/or the flow rate therethrough may be temporarily adjusted during the procedure, which may be advantageous for adjusting the way in which the various components flow through the chamber 12. For example, rather than opening the platelet-rich plasma outlet port 36 to adjust the position of the buffy coat layer C within the chamber 12, the platelet-rich plasma outlet port 36 may remain closed while the rate of flow through the open platelet-poor plasma outlet port 38 is adjusted (e.g., by adjusting the operation of a platelet-poor plasma pump acting upon tubing connected to the platelet-poor plasma outlet port 38) to adjust the position of the buffy coat layer C within the chamber 12.

5. Exemplary Multi-Phase Procedure

The preceding exemplary procedures are primarily single-phase procedures (i.e., ideally being carried out with each port of the chamber 12 being either closed or open for the entire procedure), but it is also within the scope of the present disclosure to use the chamber 12 for procedures having multiple phases, with different flow configurations during different phases (i.e., with at least one port being open to flow in a first flow configuration during a first phase and closed to flow in a second flow configuration during a second phase).

One exemplary multi-phase procedure that may be executed using a chamber 12 according to the present disclosure is a mononuclear cell collection procedure. Such a procedure may include three phases, which may be referred to as the "clean plasma collection" phase, the "main" phase, and the "harvest" phase. Other multi-phase procedures may include two phases or more than three phases, with each phase being executed once during a given procedure (a "continuous" procedure) or with one or more phases being executed more than once during a given procedure (a "cyclic" procedure).

During the "clean plasma collection" phase of the exemplary mononuclear cell collection procedure, the outlet ports are in a first flow configuration in which flow through the red blood cell outlet port 34, the platelet-rich plasma outlet port 36, and the buffy coat outlet port 40 is prevented, with blood B entering the chamber 12 via the blood inlet port 32. A platelet-poor plasma layer P separates from the cellular blood components in the chamber 12 and moves from the first lateral edge 44 of the single stage 24 toward the second lateral edge 46, where it enters into the platelet-poor plasma outlet port 38 at a radially inward position. The rate at which the platelet-poor plasma layer P flows out of the chamber 12 via the platelet-poor plasma outlet port 38 may be varied (e.g., by adjusting the operation of a platelet-poor plasma pump acting upon tubing connected to the platelet-poor plasma outlet port 38) to adjust the height of the platelet-poor plasma layer P within the chamber 12, as necessary. Alternatively (or additionally), flow through the platelet-rich plasma outlet port 36 may be temporarily allowed and adjusted to adjust the height of the platelet-poor plasma layer P within the chamber during the "clean plasma collection" phase. A portion of the platelet-poor plasma layer P exiting the chamber 12 may be conveyed to the blood source, while the remainder of the platelet-poor plasma layer P is collected.

During the "main" phase, which may be the longest of the three phases, the outlet ports are in a second flow configuration in which flow through the platelet-poor plasma port 38 and the buffy coat outlet port 40 is prevented, while flow through the red blood cell outlet port 34 and the platelet-rich plasma outlet port 36 is allowed. Blood B continues entering the chamber 12 via the blood inlet port 32. Most of the platelets in the chamber 12 will flow out of the chamber 12 via the platelet-rich plasma outlet port 36 in a platelet-rich plasma layer R, with the flow rate controlling the positions of the various separated blood component layers within the chamber 12. The separated red blood cell layer E exits the chamber 12 via the red blood cell outlet port 34, while mononuclear cells remain in the chamber 12, continuously accumulating as the "main" phase continues. The platelet-rich plasma layer R and the red blood cell layer E may be returned to the blood source.

The "harvest" phase may be carried out in a cyclic or continuous manner. In a cyclic "harvest" phase, the outlet ports are in a third flow configuration in which blood B in the chamber 12 is processed a predetermined amount of time (or a predetermined amount of blood B is processed) and then flow through the buffy coat outlet port 40 is allowed, while flow through the red blood cell outlet port 34 is prevented. Flow through the platelet-rich plasma outlet port 36 and/or the platelet-poor plasma outlet port 38 may be varied to control the position of the mononuclear cells within the chamber 12 for optimal collection efficiency of the mononuclear cells via the buffy coat outlet port 40. The mononuclear cells may be directed to a collection or storage bag or container or location, while any separated blood components exiting the chamber 12 via the platelet-rich plasma outlet port 36 and/or the platelet-poor plasma outlet port 38 may be returned to the blood source. When all or a portion of the mononuclear cells have been flowed out of the chamber 12, the procedure may revert to an earlier phase to accumulate additional mononuclear cells in the chamber 12, which is then followed by another "harvest" phase to collect an additional amount of mononuclear cells. This cycle may repeat until a target amount of mononuclear cells has been collected.

In a continuous "harvest" phase, blood B in the chamber 12 is continuously processed while flow through the platelet-rich plasma outlet port 36 is adjusted to control the location of the mononuclear cells within the chamber 12. The outlet ports are in an alternative third flow configuration in which flow through the red blood cell outlet port 34 and the buffy coat outlet port 40 is allowed, which causes the red blood cell layer E and the mononuclear cells (respectively) to exit the chamber 12. In one embodiment, flow through the blood inlet port 32, the platelet-rich plasma outlet port 36, and the buffy coat outlet port 40 is controlled via separate pumps, while the red blood cell layer E flows through the red blood cell outlet port 34 at a rate that is dictated by conservation of mass principles (i.e., the rate at which blood B is flowed into the chamber 12 less the rates at which fluid exits the chamber 12 via the platelet-rich outlet port 36 and the buffy coat outlet port 40). The mononuclear cells may be directed to a collection or storage bag or container or location, while any separated blood components exiting the chamber 12 via the red blood cell outlet port 34 and/or the platelet-rich plasma outlet port 36 may be returned to the blood source.

D. The Interface Controller

Figure 7:
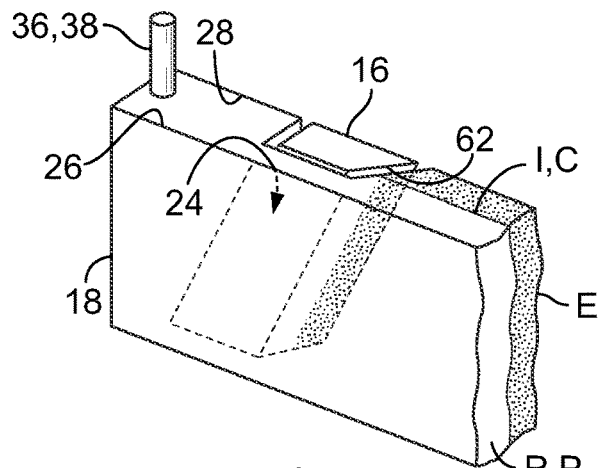
FIG. 7 is an enlarged perspective view of an interface ramp carried by the centrifuge in association with the blood separation chamber, showing the centrifugally separated red blood cell layer, plasma layer, and interface or buffy coat layer within the chamber when in a desired location on the ramp.
Figure 8:
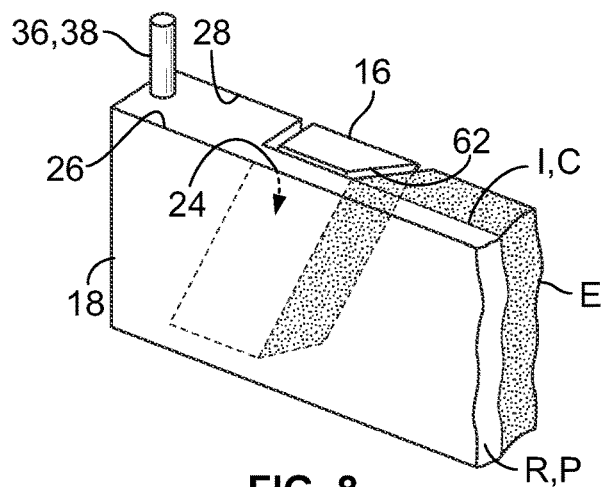
FIG. 8 shows the interface ramp of FIG. 7, with the red blood cell layer and interface or buffy coat layer at an undesired high location on the ramp.
Figure 9:
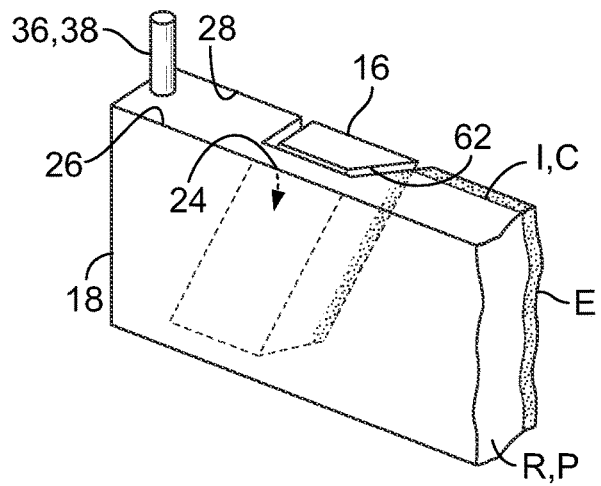
FIG. 9 shows the interface ramp of FIG. 7, with the red blood cell layer and interface or buffy coat layer at an undesired low location on the ramp.

The radial location of the buffy coat layer C (also identified as the interface I in FIGS. 7-9) can dynamically shift during blood processing. FIGS. 7-9 illustrate different possible radial locations of the buffy coat layer C or interface I between the high density component E and the low density components R and P within the single stage 24 during an exemplary separation procedure.

If the location of the interface I or buffy coat layer C is too high (that is, if it is too close to the inner wall 26, as FIG. 8 shows) or too low (that is, if it resides too far away from the inner wall 26, as FIG. 9 shows), the purity of the separated components and/or the collection efficiency of the system 10 may be impaired. Thus, it is advantageous to ensure that the interface I or buffy coat layer C is properly located within the chamber 12 (as in FIG. 7).

The different blood components have different optical properties, such that it is possible to determine the nature of a component by directing a light onto the component as it flows through the chamber 12 and/or as it flows through the tubing connected to one or more of the outlet ports. By identifying the nature of the component onto which the light is being directed, the characteristics of fluid flowing into, through, and/or out of the single stage 24 may be varied to adjust the radial position of the interface I or buffy coat layer C.

In one embodiment, a ramp is provided in combination with a light source and a light detector to determine the radial position of one or more separated components within the single stage 24. FIGS. 7-9 show an exemplary ramp 62, which extends from the inner surface of the bowl 18 toward the spool 16. FIG. 6A shows the influence of the ramp 62 on the shape assumed by a flexible-wall chamber 12 when positioned between the spool 18 and the bowl 16, with the ramp 62 extending at an angle to vertical to intersect the interior seal 48. Further details of a suitable ramp can be found in U.S. Pat. No. 5,632,893, which is incorporated herein by reference.

The ramp 62 makes the location of the interface I or buffy coat layer C more discernible for detection, displaying the locations of the various separated component layers for viewing through the outer wall 28 of the chamber 12. The blood processing system 10 may employ an interface controller, which receives data from an optical monitoring device that is indicative of the location of the interface I or buffy coat layer C on the ramp 62 and adjusts the operation of the blood processing system 10 (e.g., changing the rate at which plasma is drawn out of the blood separation chamber 12) to adjust the interface I or buffy coat layer C to the optimal location (FIG. 7).

Figure 10:
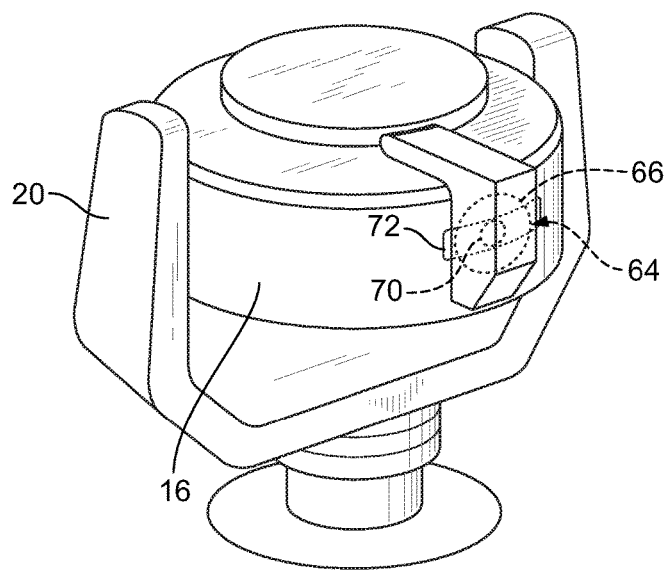
FIG. 10 is a front perspective view of the bowl and spool of the centrifuge when in the operating position, showing a viewing head, which forms a part of an interface controller, being carried by the centrifuge to view the interface ramp during rotation of the bowl.
Figure 11:
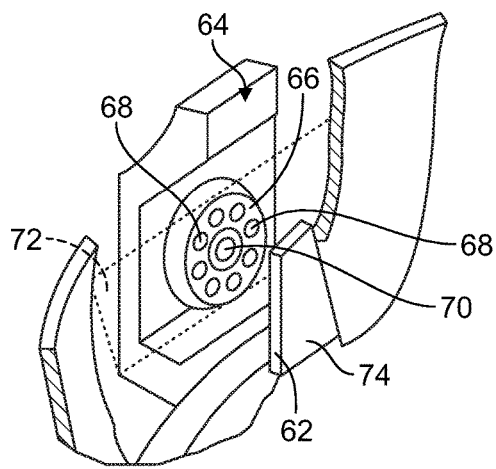
FIG. 11 is a perspective view of the viewing head of FIG. 10, with portions broken away and in section, showing the light source and light detector, which are carried by the viewing head, in alignment with the interface ramp, as viewed from within the spool and bowl of the centrifuge.
Figure 12:
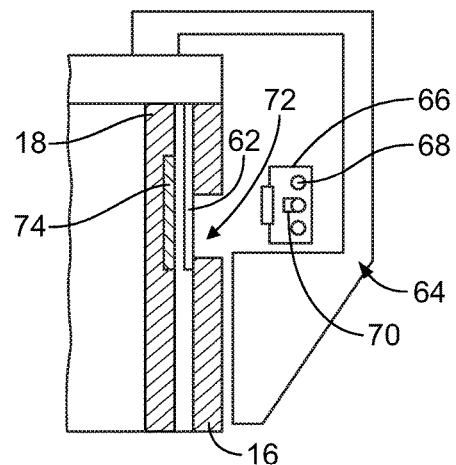
FIG. 12 is a side section view of the bowl, spool, and viewing head of FIG. 11 when the viewing head is aligned with the interface ramp.

In the illustrated embodiment, the interface controller received data from a viewing head or optical sensor assembly 64 carried on the yoke 20 (FIGS. 10-12). The optical sensor assembly 64 includes a light source 66, which emits light that is absorbed by red blood cells. In the illustrated embodiment, the light source 66 includes a circular array of red light emitting diodes 68, but other wavelengths absorbed by red blood cells, such as green or infrared, could also be used.

The illustrated optical sensor assembly 64 also includes a light detector 70, which may be mounted adjacent to the light source 66. In one embodiment, the light detector 70 comprises a PIN diode detector, which is located generally in the geometric center of the circular array of light emitting diodes 68. Other types of light detectors may also be employed. Additionally, the light detector 70 may be positioned at a different position with respect to the light source 66 (e.g., at a location radially inward of the ramp 62).

The yoke 20 and the optical sensor assembly 64 rotate at a one omega speed, as the spool 18 and bowl 16 rotate at a two omega speed. The light source 66 directs light onto the rotating bowl 16. In the illustrated embodiment, the bowl 16 is transparent to the light emitted by the light source 66 only in the region 72 where the bowl 16 overlies the ramp 62, which region may be provided as a window cut out or otherwise defined in the bowl 16. The remainder of the bowl 16 that lies in the path of the light from the optical sensor assembly 64 may comprise an opaque or light absorbing material. It should be understood that, in other embodiments, the optical sensor assembly may be placed at a stationary or zero-omega position. For example, U.S. Patent Application Publication No. 2014/0057771 (which is hereby incorporated herein by reference) describes an optical sensor assembly secured to an outer surface of the centrifuge bucket, which may be employed instead of the illustrated optical sensor assembly 64. U.S. patent application Ser. No. 14/422,188 also describes a number of possible alternative optical sensor assemblies that may be employed instead of the illustrated optical sensor assembly 64, and is hereby incorporated herein by reference.

The ramp 62 may be made of a light transmissive material. The light from the light source 66 will thereby pass through the transparent region 72 of the bowl 16 and the ramp 62 every time the rotating bowl 16 and optical sensor assembly 64 align. The spool 18 reflects incoming light received from the light source 66 out through the transparent region 72 of the bowl 16, where it is sensed by the light detector 70. The spool 18 may carry a light reflective material 74 (FIGS. 11 and 12) behind the ramp 62 to enhance its reflective properties.

As the transparent region 72 of the bowl 16 comes into alignment with the optical sensor assembly 64, the light detector 70 will first sense light reflected through a less optically dense layer (e.g., plasma) on the ramp 62. Eventually, a more optically dense layer (e.g., red blood cells) on the ramp 62 will enter the optical path of the optical sensor assembly 64. The more optically dense layer absorbs more light from the light source 66 than the less optically dense layer and thereby reduces the previously sensed intensity of the reflected light. The intensity of the reflected light sensed by the light detector 70 represents the amount of light from the light source 66 that is not absorbed by the more optically dense layer. With this information, the interface controller can determine the location of the interface I or buffy coat layer C on the ramp 62. A more detailed discussion of the algorithms by which the interface controller receives and processes signals to determine the location of the interface I or buffy coat layer C on the ramp 62 may be found in U.S. Pat. No. 6,312,607.

When the location of the interface I or buffy coat layer C on the ramp 62 has been determined, the interface controller may employ a comparator to compare the radial location output with a desired radial location and generate an error signal. The error signal may take a number of forms but, in one embodiment, is expressed in terms of a targeted red blood cell percentage value (i.e., the percentage of the ramp 62 which should be occupied by the red blood cell layer E).

When the control value is expressed in terms of a targeted red blood cell percentage value, a positive error signal indicates that the red blood cell layer E on the ramp 62 is too large (as FIG. 8 shows). In this situation, the interface controller generates a signal to adjust an operational parameter accordingly, such as by reducing the rate at which plasma is removed through the associated outlet port 36 and/or 38 under action of a system pump. Consequently, the interface I or buffy coat layer C moves away from the inner wall 26 toward the desired radial position (as FIG. 7 shows), where the error signal is zero.

A negative error signal indicates that the red blood cell layer E on the ramp 62 is too small (as FIG. 9 shows). In this situation, the interface controller generates a signal to adjust an operational parameter accordingly, such as by increasing the rate at which plasma is removed through the associated outlet port 36 and/or 38. Consequently, the interface I or buffy coat layer C moves toward the inner wall 26 to the desired radial position (FIG. 7), where the error signal is again zero.

The interface controller may include an additional optical sensor assembly associated with one or more of the tubes connected to the outlet ports, as described in greater detail in U.S. Pat. No. 8,556,793, which is incorporated herein by reference. If such a second optical sensor assembly is provided, it may monitor the associated tubing for the presence of an unexpected separated blood component (e.g., red blood cells in the tubing connected to the platelet-poor plasma outlet port 38). If an unexpected component is present in the tubing, then the operation of one or more system pumps may be temporarily modified in response to prevent further entry of the unexpected component into the outlet port or to draw the unexpected component back into the single stage 24. In one embodiment, an optical sensor assembly is associated with the buffy coat outlet port 40 or the tubing connected to the buffy coat outlet port 40 to monitor the optical density and/or color (e.g., using a colorimetric sensor) of the buffy coat layer C as it is removed from the chamber 12.

Aspects of the present subject matter described above may be beneficial alone or in combination with one or more other aspects. Without limiting the foregoing description, in accordance with one aspect of the subject matter herein, there is provided a blood separation chamber comprising a single stage defined by an inner wall including a perimeter and an outer wall including a perimeter. The inner and outer walls are joined along at least a portion of their perimeters. The blood separation chamber further includes a blood inlet port, red blood cell outlet port, platelet-rich plasma outlet port, platelet-poor plasma outlet port, and a buffy coat outlet port, all of which are connected to the single stage.

In accordance with another aspect which may be used or combined with the immediately preceding aspect, a portion of the inner and outer walls adjacent to the blood inlet port is comprised of a flexible material.

In accordance with another aspect which may be used or combined with any of the preceding aspects, a portion of the inner and outer walls adjacent to the red blood cell outlet port is comprised of a rigid material.

In accordance with another aspect which may be used or combined with any of the preceding aspects, the inner and outer walls are joined at first and second lateral edges of the perimeters. The blood inlet and platelet-rich plasma outlet ports are connected to the single stage adjacent to the first lateral edge, while the red blood cell, platelet-poor plasma, and buffy coat outlet ports are connected to the single stage adjacent to the second lateral edge.

In accordance with another aspect which may be used or combined with any of the preceding aspects, the inner and outer walls are joined at first and second axial edges of the perimeters. The blood inlet and red blood cell and platelet-rich plasma outlet ports are connected to the single stage at the first axial edge, while the platelet-poor plasma and buffy coat outlet ports are connected to the single stage between the first and second axial edges.

In accordance with another aspect which may be used or combined with any of the preceding aspects, the platelet-poor and buffy coat outlet ports are connected to the inner wall of the single stage.

In accordance with another aspect which may be used or combined with any of the preceding aspects, the blood inlet and red blood cell outlet ports open into the single stage at or adjacent to the outer wall. The platelet-rich plasma and platelet-poor outlet ports open into the single stage at or adjacent to the inner wall, while the buffy coat outlet port opens into the single stage at a position approximately midway between the inner and outer walls.

In accordance with another aspect, there is provided a method of separating blood. The method includes flowing blood into a single stage of a blood separation chamber and separating the blood in the single stage into at least first and second separated blood components. At least a portion of the first separated blood component is flowed out of the single stage by a first outlet port and at least a portion of the second separated blood component is flowed out of the single stage by a second outlet port, with flow out of the single stage by third and fourth outlet ports being prevented.

In accordance with another aspect which may be used or combined with the immediately preceding aspect, the first separated blood component comprises separated red blood cells and the first outlet port comprises a red blood cell outlet port.

In accordance with another aspect which may be used or combined with any of the preceding two aspects, the second separated blood component comprises platelet-rich plasma and the second outlet port comprises a platelet-rich plasma outlet port.

In accordance with another aspect which may be used or combined with any of the preceding three aspects, flow is temporarily allowed through at least one of the third and fourth outlet ports.

In accordance with another aspect which may be used or combined with the immediately preceding aspect, the blood in the single stage is separated into at least first, second, and third separated blood components. At least a portion of the third separated blood component is flows out of the single stage by the temporarily open third outlet port.

In accordance with another aspect which may be used or combined with the immediately preceding aspect, the third separated blood component comprises buffy coat and the third outlet port comprises a buffy coat outlet port.

In accordance with another aspect which may be used or combined with any of the preceding six aspects, the second separated blood component is flowed out of the single stage at a location positioned closer to a location at which blood is flowed into the second stage than a location at which the first separated blood component is flowed out of the single stage.

In accordance with another aspect which may be used or combined with any of the eighth through ninth aspects, the second separated blood component comprises platelet-poor plasma and the second outlet port comprises a platelet-poor plasma outlet port.

In accordance with another aspect which may be used or combined with any of the preceding eight aspects, the blood is separated in the single stage by rotating the single stage about an axis. The second separated blood component is flowed out of the single stage at a location positioned closer to the axis than the location at which the first separated blood component is flowed out of the single stage.

In accordance with another aspect, there is provided a method of separating blood. The method includes flowing blood into a single stage of a blood separation chamber and separating the blood in the single stage into first, second, and third separated blood components. At least a portion of the first separated blood component is flowed out of the single stage by a first outlet port and at least a portion of the second separated blood component is flowed out of the single stage by a second outlet port. At least a portion of the third separated blood component is flowed out of the single stage by a third outlet port, while flow out of the single stage by a fourth outlet port is prevented.

In accordance with another aspect which may be used or combined with the immediately preceding aspect, the first separated blood component comprises separated red blood cells and the first outlet port comprises a red blood cell outlet port.

In accordance with another aspect which may be used or combined with any of the preceding two aspects, the second separated blood component comprises buffy coat and the second outlet port comprises a buffy coat outlet port.

In accordance with another aspect which may be used or combined with any of the preceding three aspects, the third separated blood component comprises platelet-poor plasma and the third outlet port comprises a platelet-poor plasma outlet port.

In accordance with another aspect which may be used or combined with any of the seventeenth through nineteenth aspects, the third separated blood component comprises platelet-rich plasma and the third outlet port comprises a platelet-rich plasma outlet port.

In accordance with another aspect which may be used or combined with any of the preceding five aspects, the blood is separated in the single stage by rotating the single stage about an axis. The second separated blood component is flowed out of the single stage at a location positioned closer to the axis than the location at which the first separated blood component is flowed out of the single stage.

In accordance with another aspect which may be used or combined with any of the preceding six aspects, the blood is separated in the single stage by rotating the single stage about an axis. The third separated blood component is flowed out of the single stage at a location positioned closer to the axis than the location at which the first separated blood component is flowed out of the single stage.

In accordance with another aspect which may be used or combined with any of the preceding seven aspects, the blood is separated in the single stage by rotating the single stage about an axis. The third separated blood component is flowed out of the single stage at a location positioned closer to the axis than the location at which the second separated blood component is flowed out of the single stage.

In accordance with another aspect which may be used or combined with any of the preceding eight aspects, the blood is separated in the single stage by rotating the single stage about an axis. The second separated blood component is flowed out of the single stage at a location positioned closer to the axis than the location at which the first separated blood component is flowed out of the single stage and farther from the axis than the location at which the third separated blood component is flowed out of the single stage.

In accordance with another aspect, there is provided a method of separating blood. The method includes flowing blood into a single stage of a blood separation chamber including a blood inlet port and four outlet ports. The blood is separated in the single stage into a plurality of separated blood components. At least a portion of at least one of the separated blood components is flowed out of the single stage with the four outlet ports in a first flow configuration in which at least one of the outlet ports is open to fluid flow and at least one of the other outlet ports is closed to fluid flow. The four outlet ports are moved to a second flow configuration in which at least one outlet port which is open to fluid flow in the first flow configuration is closed to fluid flow and/or at least one outlet port which is closed to fluid flow in the first flow configuration is open to fluid flow. At least a portion of at least one of the separated blood components is flowed out of the single stage with the four outlet ports in the second flow configuration.

In accordance with another aspect which may be used or combined with the immediately preceding aspect, only one of the outlet ports is open to fluid flow in the first flow configuration.

In accordance with another aspect which may be used or combined with any of the preceding two aspects, platelet-poor plasma flows out of the single stage in the first flow configuration.

In accordance with another aspect which may be used or combined with any of the preceding three aspects, only two of the outlet ports are open to fluid flow in the second flow configuration.

In accordance with another aspect which may be used or combined with any of the preceding four aspects, platelet-rich plasma and red blood cells flow out of the single stage by different outlet ports in the second flow configuration.

In accordance with another aspect which may be used or combined with any of the preceding five aspects, the four outlet ports are moved from the second flow configuration to a third flow configuration that is different from the first and second flow configurations. At least a portion of at least one of the separated blood components is flowed out of the single stage with the four outlet ports in the third flow configuration.

In accordance with another aspect which may be used or combined with the immediately preceding aspect, mononuclear cells flow out of the single stage in the third flow configuration.

In accordance with another aspect which may be used or combined with any of the preceding two aspects, red blood cells are prevented from flowing out of the single stage in the third flow configuration.

In accordance with another aspect which may be used or combined with any of the preceding three aspects, the four outlet ports are moved from the third flow configuration to the second flow configuration after flowing at least a portion of at least one of the separated blood components out of the single stage with the four outlet ports in the third flow configuration. At least a portion of at least one of the separated blood components is flowed out of the single stage with the four outlet ports in the second flow configuration and the outlet ports are then moved from the second flow configuration back to the third flow configuration. At least a portion of at least one of the separated blood components is flowed out of the single stage with the four outlet ports in the third flow configuration.

In accordance with another aspect which may be used or combined with any of the preceding four aspects, mononuclear cells and red blood cells flow out of the single stage by different outlet ports in the third flow configuration.

In accordance with another aspect which may be used or combined with any of the preceding twenty-eight aspects, the flow rate through at least one of the outlet ports is directly controlled by a pump at the same time that flow through another one of the outlet ports is allowed without the flow rate through that outlet port being directly controlled by a pump.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood separation chamber, comprising:
   a single stage defined by an inner wall including a perimeter and an outer wall including a perimeter, wherein the inner and outer walls are joined along at least a portion of the perimeters of the inner and outer walls, including at first and second lateral edges of the perimeters;
   a blood inlet port connected to the single stage;
   a red blood cell outlet port connected to the single stage;
   a platelet-rich plasma outlet port connected to the single stage;
   a platelet-poor plasma outlet port connected to the single stage; and
   a buffy coat outlet port connected to the single stage, wherein
      the blood inlet and platelet-rich plasma outlet ports are connected to the single stage adjacent to the first lateral edge, and
      the red blood cell, platelet-poor plasma, and buffy coat outlet ports are connected to the single stage adjacent to the second lateral edge.

2. The blood separation chamber of claim 1, wherein a portion of the inner and outer walls adjacent to the blood inlet port is comprised of a flexible material.

3. The blood separation chamber of claim 1, wherein a portion of the inner and outer walls adjacent to the red blood cell outlet port is comprised of a rigid material.

4. The blood separation chamber of claim 1, wherein
   the inner and outer walls are joined at first and second axial edges of the perimeters,
   the blood inlet and red blood cell and platelet-rich plasma outlet ports are connected to the single stage at the first axial edge, and
   the platelet-poor plasma and buffy coat outlet ports are connected to the single stage between the first and second axial edges.

5. The blood separation chamber of claim 1, wherein the platelet-poor and buffy coat outlet ports are connected to the inner wall of the single stage.

6. The blood separation chamber of claim 1, wherein
   the blood inlet and red blood cell outlet ports open into the single stage at or adjacent to the outer wall,
   the platelet-rich plasma and platelet-poor outlet ports open into the single stage at or adjacent to the inner wall, and
   the buffy coat outlet port opens into the single stage at a position approximately midway between the inner and outer walls.

7. The blood separation chamber of claim 1, wherein
   the blood inlet and platelet-rich plasma outlet ports are connected to the single stage adjacent to a region of the single stage into which blood is introduced, and
   the red blood cell, platelet-poor plasma, and buffy coat outlet ports are connected to the single stage adjacent to an end of the single stage opposite to said region into which blood is introduced.

* * * * *